United States Patent
Roura Fernandez et al.

(10) Patent No.: US 9,572,749 B2
(45) Date of Patent: Feb. 21, 2017

(54) DEVICE FOR TAKING SAMPLES FROM CONTAINERS

(71) Applicant: GRIFOLS WORLDWIDE OPERATIONS LIMITED, Dublin (IE)

(72) Inventors: Carlos Roura Fernandez, San Juan Despi (ES); Manuel Garcia Sanchez, Barcelona (ES); Daniel Fleta Coit, Bigues (ES)

(73) Assignee: GRIFOLS WORLDWIDE OPERATIONS LIMITED, Dublin (IE)

( * ) Notice: Subject to any disclaimer, the term of this patent is extended or adjusted under 35 U.S.C. 154(b) by 0 days.

(21) Appl. No.: 14/616,588

(22) Filed: Feb. 6, 2015

(65) Prior Publication Data

US 2015/0224027 A1   Aug. 13, 2015

(30) Foreign Application Priority Data

Feb. 7, 2014   (ES) .................... 201430162

(51) Int. Cl.
| | |
|---|---|
| *A61J 1/12* | (2006.01) |
| *A61J 1/16* | (2006.01) |
| *B65C 3/12* | (2006.01) |
| *G01N 35/10* | (2006.01) |
| *B65B 3/00* | (2006.01) |

(Continued)

(52) U.S. Cl.
CPC .. *A61J 1/12* (2013.01); *A61J 1/16* (2013.01); *B01L 9/06* (2013.01); *B65B 3/003* (2013.01); *B65C 3/105* (2013.01); *B65C 3/12* (2013.01); *G01N 35/1011* (2013.01); *G01N 35/1079* (2013.01); *B01L 3/5453* (2013.01);

(Continued)

(58) Field of Classification Search
CPC ............ G01N 35/1011; G01N 35/1079; G01N 2035/00861; B01L 2300/0672; B65B 3/003; A61J 1/12; A61J 1/14
See application file for complete search history.

(56) References Cited

U.S. PATENT DOCUMENTS

| | | |
|---|---|---|
| 2007/0134131 A1 | 6/2007 | Watson et al. |
| 2008/0169043 A1 | 7/2008 | Osborne et al. |

FOREIGN PATENT DOCUMENTS

| | | |
|---|---|---|
| EP | 0 502 638 A2 | 9/1992 |
| EP | 1525918 A2 | 4/2005 |

(Continued)

OTHER PUBLICATIONS

European Search Report dated Jun. 19, 2015 of corresponding European Patent Application No. 15154088.7—13 pages.

(Continued)

*Primary Examiner* — Brian R Gordon
(74) *Attorney, Agent, or Firm* — Knobbe Martens Olson and Bear, LLP

(57) ABSTRACT

A device for taking samples from containers includes: a receiving body for at least one container; a container bar code reader positioned in the receiving body for containers; a support for a test tube with the ability to move; a bar code reader positioned in the support; and a fluid communication component between the container and the test tube. The support for test tubes includes at least a test tube loading position and a sample-taking position. The device also includes a controller configured to control position of the support for test tube. The controller can also include at least one sensor of the position of the support for test tube and a blocking component configured to block a position of said support for test tube.

8 Claims, 6 Drawing Sheets

(51) Int. Cl.
*B65C 3/10* (2006.01)
*B01L 9/06* (2006.01)
G01N 35/00 (2006.01)
B01L 3/00 (2006.01)

(52) U.S. Cl.
CPC ... *B01L 2200/143* (2013.01); *B01L 2300/021* (2013.01); *G01N 2035/00861* (2013.01)

(56) References Cited

FOREIGN PATENT DOCUMENTS

EP      2 209 007 A2     7/2010
EP      2 439 143 A1     4/2012

OTHER PUBLICATIONS

Search Report issued in Spanish Application No. 201430162, filed Feb. 7, 2014.

DEVICE FOR TAKING SAMPLES FROM CONTAINERS

BACKGROUND

The present disclosure relates to a device for taking samples, in particular, the present disclosure relates to a device for sampling collection containers (e.g. bottles of plasma) by means of test tubes for vacuum-extraction of samples.

At present, various devices exist for taking samples, including some completely automatic systems such as the device disclosed in European patent EP 2209007, for example. This device comprises a housing for containers, an input housing for multiple test tubes and the device is loaded automatically by taking each of the tubes, labelling them, taking the samples and placing the sealed, labelled test tube containing the sample at one of the outputs thereof.

These devices are technically complex with a wide variety of position sensors, cameras, image recognition systems and other peripheral devices that are required to ensure correct transfer of the fluids from the container to the test tube. This technical complexity and the need for coordination between the various peripheral devices result in this device being of considerable size and, in addition, requiring staff who specialise in robotic equipment to maintain them properly as well as providing technical support for the user personnel.

SUMMARY

This disclosure relates to a device in which some of these processes have been converted from automatic to manual processes to reduce the technical complexity of the equipment and its size.

Surprisingly, this reduction in the number of the technical elements signifies greater flexibility in the device and allows staff with no high-level technical specialisation to carry out maintenance tasks on the equipment thus maintaining its reliability.

Specifically, this disclosure relates to a device for taking samples from containers which comprises:
a receiving body for at least one container;
a container bar code reader associated with the container positioned in the receiving body for containers;
a bar code reader associated with the test tube positioned in the test tube support;
a support for at least one test tube with the ability to move; and
fluid communication channel between the container and the test tube;
in which the support for test tubes comprises at least a loaded tube position and a sample-taking position, said device comprising controller (means for controlling) of the position of the test tube support which, in turn, comprise at least one test tube support position sensor and means for blocking the position of said test tube support.

In a particularly embodiment, the positions of the device comprise at least:
a loaded tube position: this is a position in which the test tube is disconnected from the fluid communication means (channel) between the container and the test tube;
a sample-taking position: this is a position in which the test tube is connected to the fluid communication means between the container and the test tube, allowing fluids to pass from the container to the test tube.

Preferably the user carries out said movement between said positions manually.

In addition, there may be intermediate positions of the device such as an intermediate position, for example, in which the container label has already been read and a check has been performed to ensure that the container label correlates to the test tube label.

More preferably, the function of correlating the bar code read from the test tube with the bar code read from the container is carried out by the controller (means to control) of the position of the support for test tubes.

In addition, said means to control the position of the support actuate or de-actuate said blocking means.

In a particular embodiment, the device has at least a first position sensor in the loaded tube and a second position sensor in the sample-taking position.

These are preferably end-of-travel sensors although in some embodiments of the present invention micro switches, Hall-effect sensors or infrared sensors are used, among others.

Still more preferably, the ability of the test tube support to move is limited to a longitudinal movement with respect to the test tube, this movement taking the test tube towards a puncturing element which is also longitudinal to the tube, which reduces the effective space required by the device.

In an embodiment of the present invention, the test tube is a vacuum test tube and the fluid communication means between the test tube and the container may comprise means for puncturing the test tube. Thus, when punctured, the vacuum in the test tube extracts a sample from the container by suction.

In a certain embodiment, the device comprises a bar code label printer; in this way the apparatus can print a label with a bar code that corresponds to the bar code read by the bar code reader associated with the container, reducing the possibility of human error in the process.

With the objective to have the possibility to inform the user of which phase the filling procedure has reached, the device according to a certain embodiment of the present invention comprises means for signalling the loaded tube position and/or the sample-taking position of the container. Preferably, said signalling means (signalling component) are associated at least with the position sensors.

Alternatively, said signalling means are also associated with at least one of the bar code readers.

In addition, an embodiment of the device according to a certain embodiment of the present invention comprises a mechanism for sticking labels to the test tube. Said label sticking mechanism may comprise two rollers, one on either side of the test tube. Preferably, one of the rollers rotates freely while the other is connected to an actuator so that the user can rotate it.

In particular, said label sticking mechanism is positioned in the test tube support.

For a better understanding, and as an explanatory but not limiting example, the accompanying drawings of an embodiment of the device a certain embodiment of according to the present invention are provided.

DETAILED DESCRIPTION

Figure 1:
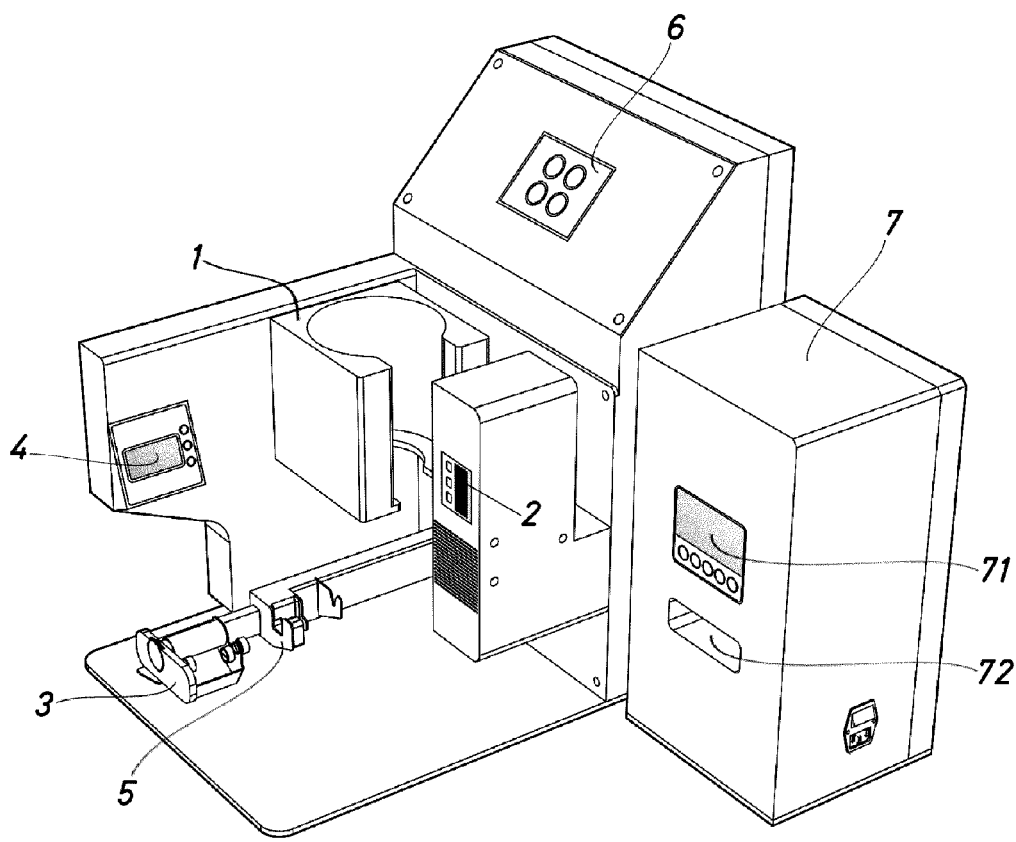
FIG. 1 is a perspective view of an embodiment of the invention by way of example.

FIG. 1 shows a device for taking samples from containers, that is, a device for taking samples in test tubes from larger containers, for example, bottles of plasma.

The device in the embodiment shown by way of example in FIG. 1 comprises a receiving body 1 for containers, a support 3 for test tubes, a housing 5 for fluid communication channel between the container and the test tube, these fluid communication channel being responsible for the transfer of some of the fluids located in the container to the test tubes.

The device of FIG. 1 also shows a first bar code reader 2 for reading the labels of the containers and a second bar code reader 4 for reading the labels of the test tubes.

Furthermore, the device shown in FIG. 1 comprises a panel 6 on which the operating commands and/or lights indicating the current operational state of the device are located. In this embodiment, a bar code label printer 7 which has an operating panel 71 and a label output 72 is also included, although said printer is optional.

Figure 2:
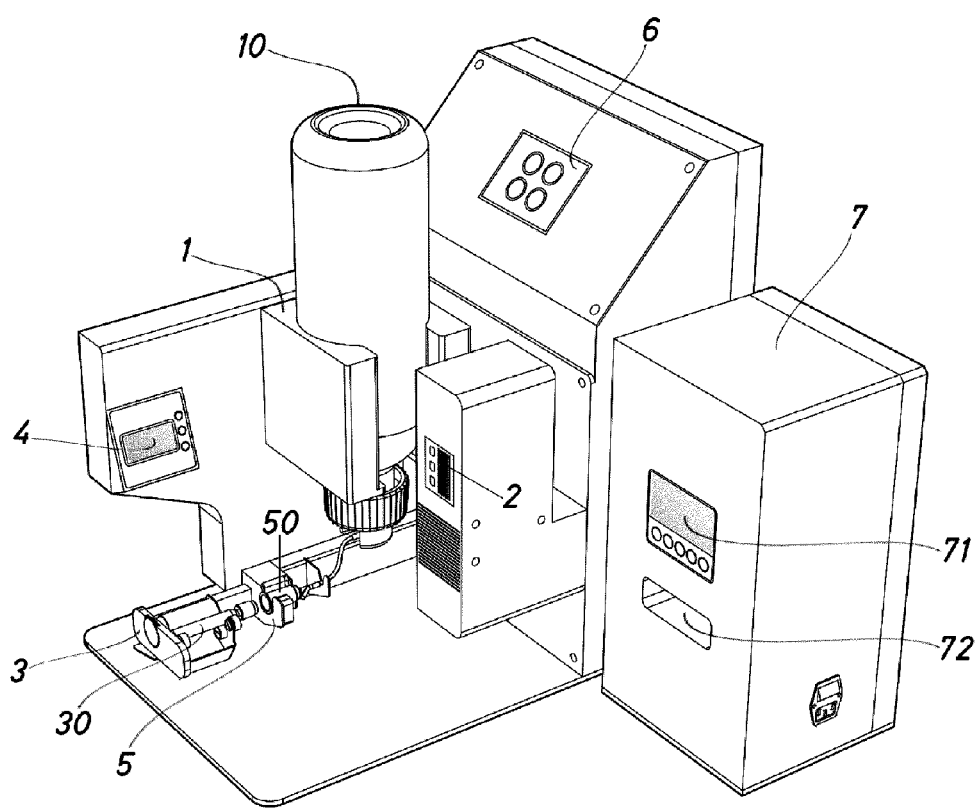
FIG. 2 is a perspective view of the embodiment of FIG. 1 with the container, the test tube and the fluid communication channel between the test tube and the container arranged on the device.

FIG. 2 shows the arrangement of the elements for taking samples on the device of FIG. 1.

In particular, a container 10 arranged in the receiving body 1 for containers, a test tube 30 arranged in the test tube support 3 and the fluid communication means (channel) 50 between the container 10 and the test tube 30 arranged in its respective housing 5 can be seen.

The operation of the device of FIG. 2 is based on the controlled movement of the support 3 for test tubes. In this particular embodiment, the support 3 for test tubes 30 has the ability to move longitudinally with respect to the tube 30, that is, it moves the tube 30 towards the fluid communication means 50 between the container 10 and the tube 30. These fluid communication means 50 may comprise means for puncturing the mouth of the tube 30, for example, by means of a hollow needle which allows fluids to pass through said needle towards the tube.

Said controlled movement occurs by controlling various process variables, for example, by sensors and having actuators to prevent movement should the conditions laid down not be fulfilled.

Specifically, a certain embodiment the present invention provides the arrangement of mechanisms for controlling the process of sample taking by the device, even in embodiments in which the support for the test tubes is moved by manual means.

These mechanisms are, for example, a first position sensor of the test tube in the support, said sensor possibly being a micro switch or a magnetic sensor, among others. A second mechanism may be the detection of a correlation between the reading on the one hand of the bar codes read by a bar code reader 2 and, on the other hand, of the bar code reader 4 of the test tube.

Furthermore, in particular embodiments of the present invention, the tube is a vacuum tube of which the mouth is sealed by a material, preferably an elastomer material. In this way puncturing the tube produces a fluid communication channel between the tube and the container with a difference in pressure between said tube and said container. This difference in pressure causes the fluids to be transferred from the container to the test tube by suction.

The device of FIG. 2 also shows a panel 6 with various indicator lights showing the status of the device, in other words, whether the test tube is loaded, whether all the elements external to the device, and which are needed to perform the sample-taking process, are positioned (such as containers, test tubes and communication means between containers and test tubes), whether the containers and test tubes are correctly correlated, whether the device is in the sample-taking position or the rest position, etc.

In particular, the device of FIG. 2 has four indicators on its panel 6: a first indicator which shows whether the device is switched on, a second indicator which shows whether there is a correlation between the bar codes of the container and the test tube, a third indicator which shows whether the test tube is in the loaded tube position (i.e., disconnected from the fluid communication means between the container and the test tube) and a fourth indicator which shows whether the test tube is in the sample-taking position (connected to the communication means).

Moreover, additional indicators can be provided, or a different colour can be used, for example, for each of the indicators to signal possible alerts such as a green colour for the fourth indicator light used intermittently to indicate that the tube is loading a sample, said indicator light remaining constant once the average loading time (approximately, 3 seconds) has passed, but should a read error occur said indicator can change to red.

Figure 3:
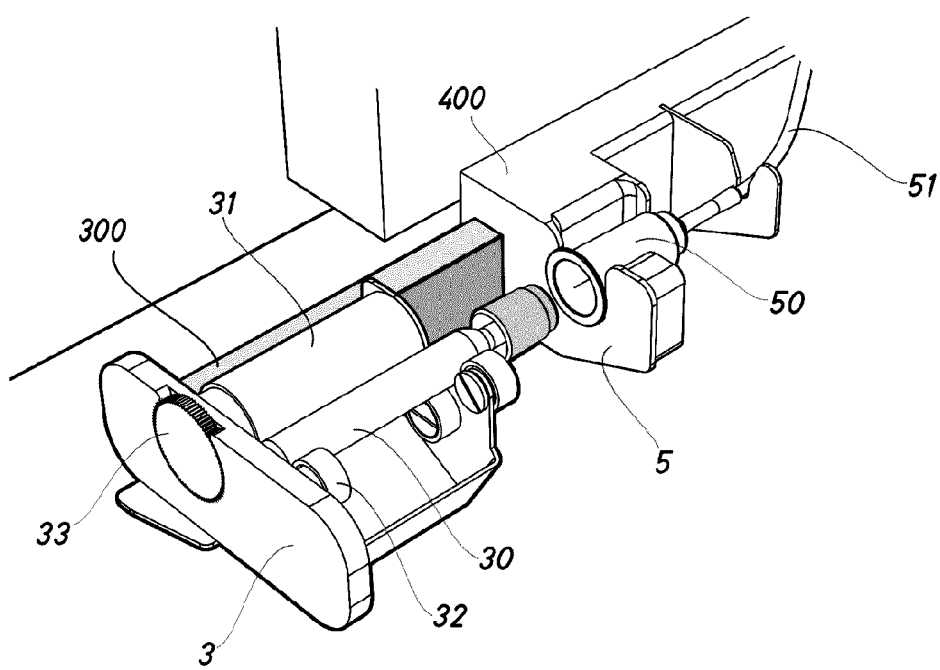
FIG. 3 is an enlarged perspective view of the test tube support of the device of FIG. 2.

FIG. 3 shows in detail the test tube receptacle 3. This support 3 comprises a pair of rollers 31, 32, between which the test tube is arranged. In this particular embodiment, the support 3 comprises a first roller 31 associated with an actuator 33 and a free roller 32 of which the function is principally to keep the test tube pressed against the first roller 31. The user uses the actuator 33 to rotate the first roller 31, and it could be used for example to stick a label with a bar code to the test tube 30 or simply to align a bar code that had previously been stuck to the test tube 30 with a bar code reader.

The support 3 in FIG. 3 comprises a projection 300 combined with a guide 400 for the device. Said projection 300 moves on said guide preferably in a longitudinal direction to the test tube 30 so that said test tube 30 moves closer to the fluid communication means 50 between the container 10 and the tube 30.

Figure 4:
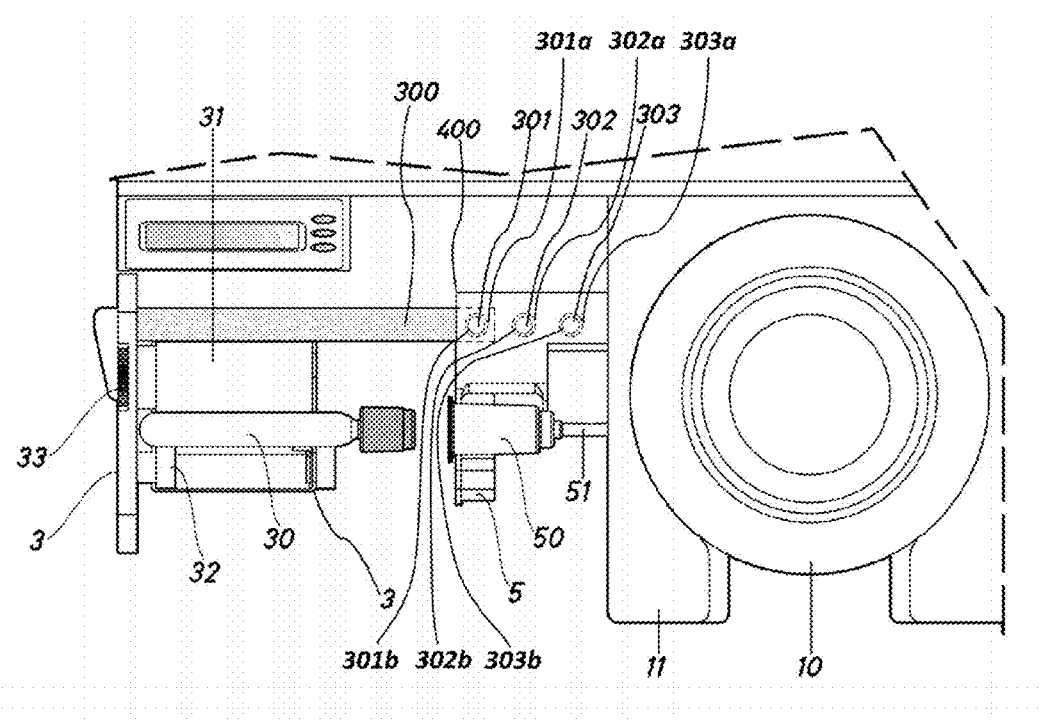
FIG. 4 is a partial plant view of the device of FIG. 2.

FIG. 4 is a top view of FIG. 3. The support 3 control elements and movement detection elements are shown in this figure.

In particular, it can be seen that elements are provided associated with the guide 400 for detecting the position of the projection 300 of the receptacle 3. Since the projection moves together with the receptacle (and consequently in conjunction with the test tube 30), the a certain embodiment of present invention provides the arrangement of sensors and mechanisms for blocking the projection 300 to prevent or allow it to move along the guide.

For this reason, three control points are provided: a first point 301 corresponding to the position in which the test tube 30 is loaded, in which the test tube 30 is farther away from the fluid communication means 50 between the container 10 and the test tube 30; a second control point 302 in which the support has moved from the test tube 30 loaded position and is at an intermediate point of travel; and a third control point 303 corresponding to the sample-taking position in which the test tube 30 has been perforated by the needle of the fluid communication means 50 defining a channel for fluids to pass between the container 10 and the test tube 30.

In a particular embodiment, a sensor 301a-303a is arranged at each of the control points to detect the presence of the projection 300 and a blocking mechanism 301b-303b to prevent said projection from moving if predefined conditions are not fulfilled, such as correspondence between the labels of the test tube and the container, the presence of test tubes in the receptacle, etc.

However, particular embodiments of the present invention comprise sensors only at some control points and blocking means (blocking component) 301b-303b at some of those control points. In other embodiments, the blocking points do not coincide exactly with the points where the sensors 301a-303a are located. Said embodiments are also considered to fall within the protective scope of the present invention.

Figure 5:
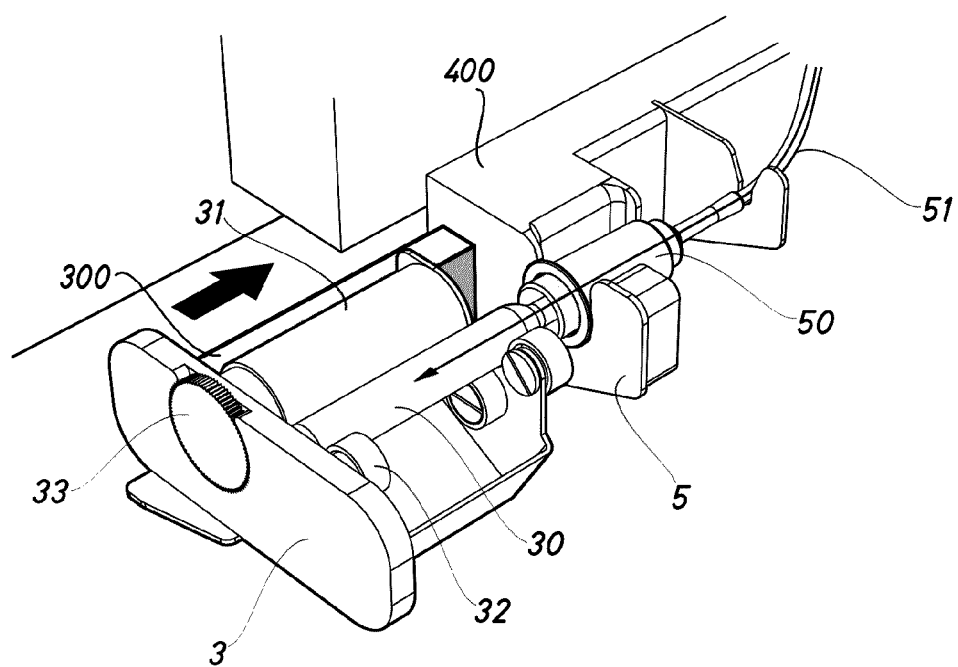
FIG. 5 is an enlarged perspective view of the test tube support of the device of FIG. 2 moved to the sample-taking position.

FIG. 5 is an enlarged perspective view of the support 3 for test tubes 30 when said support 3 is in the sample-taking position.

It can be seen in FIG. 5 that when the test tube 30 comes in contact with the fluid communication means 50 between the test tube 30 and the container 10 there is a flow of fluids through the flexible tube 51 when the test tube 30 is perforated by the fluid communication means 50 by means of a hollow needle. Therefore, the change of position of the receptacle 3 of the test tubes 30 from the loaded tube position to the sample-taking position allows fluids to pass from the container 10 by means of a flexible tube 51 and through the hollow needle.

Figure 6:
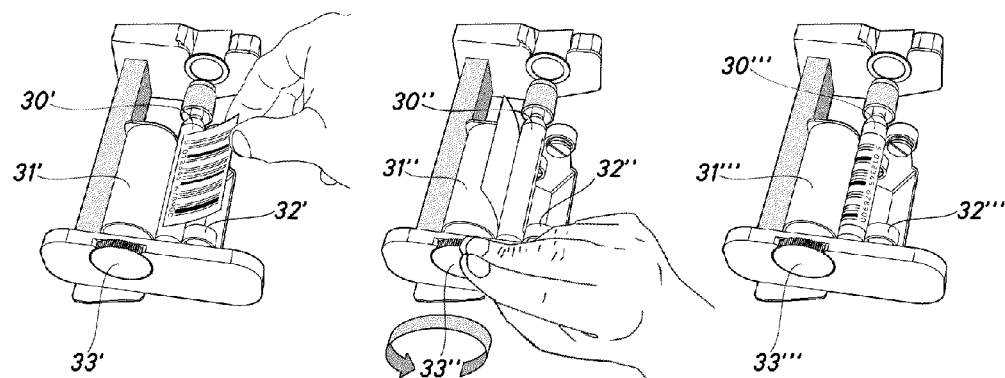
FIG. 6 illustrates three of the phases of the process of sticking labels to the test tubes in the test tube support.

FIG. 6 shows three figures corresponding to three phases of the process of placing a label on a test tube arranged in a support for test tubes.

The first figure shows how the test tube 30' is placed in a first step between the rollers 31' and 32'. Preferably, the free roller 32' has the ability to move transversally with respect to the test tube and is actuated by a elastomeric component such as a spring, for example, which applies a force to the free roller 32' in the direction of the roller 31' connected to the actuator 33'. The arrangement of the test tube 30' between the rollers 31', 32' moves the free roller 32' slightly away from the roller 31' connected to the actuator, the test tube 30' being held between the two rollers by the action of said spring. Once the tube is arranged in the support, a portion of the label is stuck to the test tube.

The second figure shows how subsequently the actuator 33" is rotated which, in turn, causes the roller 31" and the test tube 30" to rotate. The force applied by the free roller 32" causes the roller 31" to come in contact uniformly with the entire surface of the tube 30" as the actuator 33" rotates until the label is completely stuck to the test tube.

The third figure shows how, once the label has been stuck, the actuator 33''' can be used to rotate the test tube 30''' to a position in which the label is visible, for example, to the bar code readers without having to remove the test tube 30''' from the support 3'''.

Although the invention has been described with regard to example embodiments, said examples should not be considered to limit the invention, which is defined by the widest interpretation of the following claims.

What is claimed is:

1. A device for taking samples from containers, the device comprises:
    a container for containing a substance, the container having a first bar code thereon;
    a body holding the container;
    a first bar code reader facing the container and configured to read the first bar code of the container;
    a cannula capable of being connected to and disconnected from the container;
    a housing holding the cannula connected to the container;
    a linear guide fixed to the housing;
    a test tube for receiving the substance from the container, the test tube having a second bar code thereon;
    a support configured to move along the linear guide and holding the test tube, wherein the support is configured to move between a first position and a second position that is closer to the housing than the first position such that the test tube is separated from the cannula at the first position and the test tube is connected with the container via the cannula at the second position;
    a second bar code reader facing the test tube and configured to read the second bar code of the test tube; and
    a blocking component placed at a point of the linear guide between two points corresponding to the first and second positions of the support, wherein the blocking component is configured to block movement of the support between the first position and the second position when the first bar code does not match to the second bar code.

2. The device according to claim 1, wherein the device is further configured to correlate the second bar code of the test tube with the first bar code of the container.

3. The device according to claim 1, wherein the device further comprises a first position sensor configured to detect presence of the support at a first control point of the linear guide and a second position sensor configured to detect presence of the support at a second control point of the linear guide.

4. The device according to claim 1, wherein the test tube extends in a first direction relative to the support, and the support is configured to move along the linear guide in a second direction that is opposite to the first direction.

5. The device according to claim 1, wherein the test tube is a vacuum test tube.

6. The device according to claim 1, wherein the cannula comprises a puncturing component configured to puncture the test tube when the support is at the second position.

7. The device according to claim 1, further comprising a controller configured to actuate or de-actuate the said blocking components.

8. A method for taking sample using the device of claim 7, the method comprising:
    reading, by the first bar code reader, the first bar code on the container;
    reading, by the second bar code reader, the second bar code on the test tube container that is held by the support; and
    determining, by the controller, whether the first bar code matches the second barcode,
    wherein if it is determined that the first bar code does not match the second bar code, the controller actuates the blocking component to restrict movement of the support, such that the test tube is not connected to the container via the cannula,
    wherein if it is determined that the first bar code matches the second bar code, the controller de-actuates the blocking component to allow movement of the support, such that the test tube can be connected to the container via the cannula.

* * * * *